United States Patent [19]

Seifert

[11] Patent Number: 5,035,348

[45] Date of Patent: Jul. 30, 1991

[54] CONTAINER HAVING A PRESSURE-RUPTURABLE SEAL FOR DISPENSING CONTENTS

[75] Inventor: Robert P. Seifert, Wolfeboro, N.H.

[73] Assignee: Institute Guilfoyle, Belmont, Mass.

[21] Appl. No.: 402,084

[22] Filed: Sep. 1, 1989

[51] Int. Cl.⁵ ............................................. B65D 47/10
[52] U.S. Cl. .................................. 222/107; 222/189; 222/541; 401/132
[58] Field of Search ................ 222/107, 541, 189, 92, 222/491, 212, 213; 206/219; 401/132

[56] References Cited

U.S. PATENT DOCUMENTS

| | | | |
|---|---|---|---|
| 2,430,995 | 11/1947 | Roos | 222/107 |
| 2,663,461 | 12/1953 | Brown | 222/107 |
| 3,334,790 | 8/1967 | Eaton | 222/107 |
| 3,601,252 | 8/1971 | Sager | 222/107 |
| 3,757,782 | 9/1973 | Aiken | 222/107 X |
| 3,913,789 | 10/1975 | Miller | 222/107 |
| 3,964,604 | 6/1976 | Prenntzell | 206/219 |
| 4,759,472 | 7/1988 | Strenger | 222/541 |
| 4,890,744 | 1/1990 | Lane, Jr. et al. | 222/541 X |

FOREIGN PATENT DOCUMENTS 0078761  5/1983  European Pat. Off. ............ 222/541

Primary Examiner—Kevin P. Shaver
Attorney, Agent, or Firm—Cesari & McKenna

[57] ABSTRACT

A flexible fluid dispenser includes a flexible fluid-containing vessel which has a seal which seals a top wall of the vessel to a bottom wall and is shaped to concentrate in a region thereof forces resulting from pressure generated by applying a force to the dispenser. When the resulting force is sufficiently large, the weaker top or bottom wall of the vessel breaks, or opens, at the concentration region of the seal. The opening has dimensions which approximate the dimensions of the force-concentrating region of the seal.

7 Claims, 1 Drawing Sheet

CONTAINER HAVING A PRESSURE-RUPTURABLE SEAL FOR DISPENSING CONTENTS

FIELD OF INVENTION

This invention relates generally to fluid dispensers, and more particularly to disposable, flexible fluid dispensers.

BACKGROUND OF THE INVENTION

Disposable, flexible plastic or glass fluid dispensers are currently used to dispense all sorts of liquid, or liquid-like, substances. For example, take-out food restaurants offer ketchup and mustard to their customers in disposable plastic dispensers which resemble rectangular pouches, and cosmetic manufacturers offer their customers one-application samples of various products such as shampoo, moisturizer, etc., in disposable plastic or glass flexible dispensers. Similarly, pharmaceutical companies distribute medications, such as liquid vitamins or ointments, in disposable one-dosage dispensers.

The user opens the dispensers by splitting, cutting or puncturing them. Depending on the design of the dispenser, the user may open it by cutting or ripping off a particular section of it, typically along a perforation, puncturing it with a sharp object, or squeezing it until it pops open. Often, when a user rips the dispenser along a perforation, he or she simply pulls off a section of the dispenser without opening it. The user then must squeeze the dispenser to further split it, all the while hoping that the contents of the dispenser do not spray out in all directions through the perforations.

A user who attempts to open a dispenser by puncturing it may end up spewing the contents in unpredictable and often uncontrollable directions. For example, a user attempting to puncture a dispenser at a particular spot may inadvertently squeeze the dispenser with enough force to split it at a different, and often unexpected, spot. The contents of the dispenser may then spill out through the split. Many take-out food customers share the experience of inadvertently splitting a ketchup dispenser and spilling the ketchup all over themselves. If, instead of ketchup, the dispenser contains a liquid medication or a reactive chemical, the consequences of spraying the contents may be serious. What is needed is a disposable dispenser which opens at a predictable spot in a predictable manner.

The unpredictable dispensers present users with a second, related problem, namely, the problem of controlling the amount of liquid which emerges from the dispenser once it is opened. For example, when a user squeezes a dispenser to open it, he or she may squeeze with enough force to cause a relatively large amount of fluid to spurt out of the dispenser through the opening. Similarly, once the dispenser is opened, a later squeeze may result in the dispensing of a large amount of the fluid when the person squeezing the dispenser requires only a small amount. What is needed is a dispenser which releases its liquid contents in a controllable manner.

SUMMARY

The invention is a flexible fluid dispenser which has at one end a seal shaped to distribute forces generated by pressure inside the vessel and at the other end a seal shaped to focus the forces generated by the pressure. When a user squeezes the vessel to open it, the vessel opens, or fails, at the force-focusing seal. Thus the vessel has a predictable failure point.

In a preferred embodiment, the vessel has at one end a substantially linear seal and at the other end an inwardly-pointing "V-shaped" seal. The apex of the V-shaped seal points toward the center of the vessel. When a user squeezes the vessel to open it, the resulting forces generated inside the vessel are focused at the apex of the inwardly-pointing V-shaped seal. Thus the vessel opens at the seal apex, and the opening is approximately the size of the apex.

Another dispenser embodying the invention has, in addition to end seals, a third force-focusing seal proximate to one end. The third seal may be of any shape, however, the periphery of this seal should be small so as to ensure that the stresses in this seal caused by pressure within the vessel are greater than the stresses in the vessel walls and the end seals. When a user squeezes this vessel to open it, the vessel opens at this third seal. The opening is approximately the size of the third seal.

The various seals may be formed using any conventional sealing method. However, heat sealing is the preferred method of forming the force-focusing seal. To form this seal, a heat seal mechanism presses corresponding sections of each side of the vessel between a selectively heated platen and an unheated platen. The heat from the heated platen melts the vessel material and the two sides fuse together to form the seal. The material closest to the heated platen melts more than the material which is closest to the unheated platen. Accordingly, when the two platens are pressed together they flatten and thin one side of the seal more than the other, and the seal has one side which is weaker than the other. When a user squeezes the vessel to open it, it opens, or fails, on this weaker side.

BRIEF DESCRIPTION OF THE DRAWINGS

For a more complete understanding of the features, advantages, and objects of the invention, reference should be made to the following detailed description and the accompanying drawings, in which.

DETAILED DESCRIPTION

Figure 1:
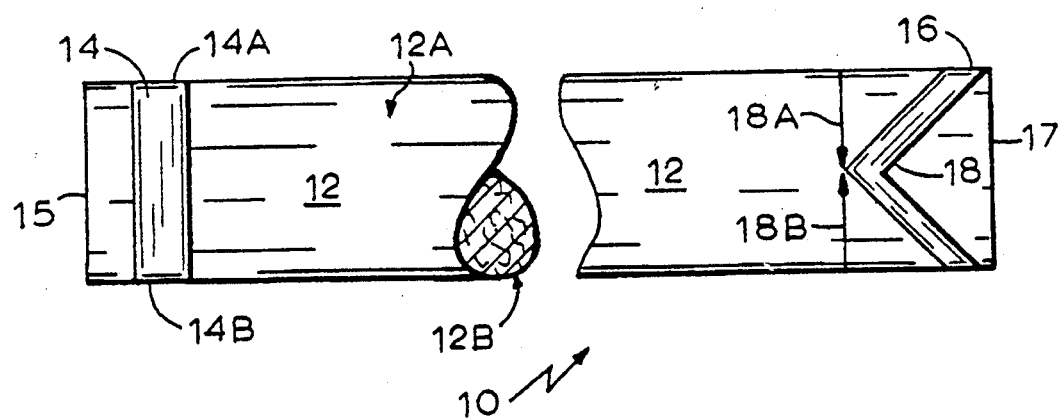
FIG. 1 is an illustration of a dispenser constructed in accordance with the preferred embodiment of the invention.

As shown in FIG. 1, a dispenser 10 constructed in accordance with the preferred embodiment of the invention includes a vessel 12 having a substantially linear heat seal 14 at an end 15 and an inwardly-pointing "V-shaped" heat seal 16 at an opposite end 17. The inwardly-pointing V-shaped seal 16 is oriented such that the seal apex 18 points toward the substantially linear seal 14. The dispenser 10 is made of a relatively flexible substance, for example, a plastic such as polyethylene.

In order to store liquid in the dispenser 10, the vessel 12 is first sealed at one end, for example, end 17, by a heat sealer (not shown). Next, liquid is poured into the vessel 12 and the open end 15 of the vessel 12 is sealed. Thus the heat sealer first applies heat to the end 17 to form the inwardly-pointing V-shaped seal 16 and then applies heat to the end 15 to form the substantially linear seal 14. The heat sealer forms each of the seals 14 and 16 in a conventional manner, that is, by applying a selectively heated platen to an appropriate section of one side 12A of the dispenser and an unheated platen to the opposite side 12B. The platens are then clamped together to form the seal 14 or 16.

The characteristics of the material next to the heated platen differ from those of the material next to the unheated platen due to differences in the melting of the two sides. The material next to the heated platen (side 12A) melts more than the material next to the unheated platen (side 12B). When the two sides are clamped together to form the seal, the material closest to the heated platen (side 12A) flattens, and thus thins, more than the material on the other side. Accordingly, the seal has one side which is thinner and consequently weaker than the other side. When sufficient pressure is applied to the vessel, it is this weaker side which opens, or fails.

Due to the overall structure of the dispenser 10, and more particularly the use of the inwardly-pointing V-shaped seal 16 on one end, the dispenser 10 opens predictably at apex 18. When the user squeezes the midsection of the dispenser 10 stresses are generated in the dispenser 10. These stresses are distributed over the seals 14 and 16. Thus the stresses to which linear seal 14 is subjected are distributed evenly across the seal from 14A to 14B. However, as a result of the geometry of the V-shaped seal, the stresses to which seal 16 is subjected are greatest at the apex 18.

The stresses on the seals are equal to the force per unit area. The force is proportional to the cross-sectional area, that is the area between the side-walls of the vessel and the seal. The cross-sectional area is greatest at the apex 18 as indicated by arrows 18A and 18B. Thus the apex 18 of seal 16 is subjected to more stress than any other point of the seal 16 or any one point of seal 14. It is the apex 18 which fails, or opens, first when the dispenser 10 is squeezed. As discussed above, the apex 18 fails where it is weakest or thinnest (side 12A), i.e., fails on the side which had been next to the heated platen.

To open the dispenser 10, a user squeezes vessel 12 at a point in between the two seals 14 and 16. When the applied pressure is large enough to generate a sufficient force inside the vessel, the dispenser 10 fails, or opens, at the apex 18 of the inwardly-pointing V-shaped seal 16 on side 12A. The force required to open the dispenser 10 varies depending on the size and shape of the dispenser 10, and the material out of which it is constructed. However, before a user squeezes the dispenser 10, he or she knows where the dispenser 10 will open, and he or she can accurately control the dispensing of the contained fluid.

The seal 14 may be of any shape, as long as it operates to distribute the internal forces. Thus, the seal 14 may be "C-shaped" or at an angle with respect to a center axis.

The various seals may be formed using any conventional sealing method with the same result, which is that the dispenser 10 opens at the apex 18. If the side on which the dispenser opens is important to the user, conventional methods of rendering one side of the seal weaker than the other may be used to ensure that the failure point is on a particular side of the dispenser. For example, if seal 16 is a cement seal, the material on one side of the dispenser may be thinner than the material on other, at least at the point of the seal. Similarly, for a cement seal 16, one side of the dispenser may be made of a material which absorbs the cement while the other side is made of a material which does not. When the seal forms the material on the side which absorbs the cement is thinner, and thus, the seal is weak on this side.

Figure 2:
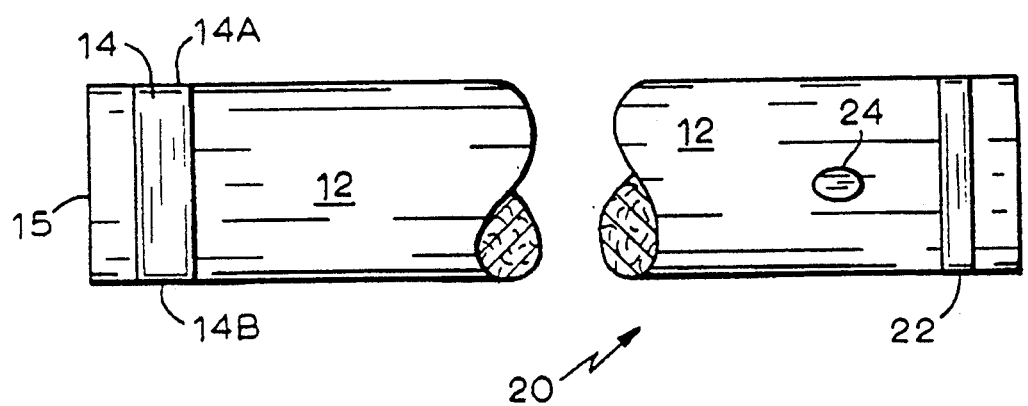
FIG. 2 is an illustration of a dispenser constructed in accordance with a second embodiment of the invention.

FIG. 2 illustrates a dispenser 20 constructed in accordance with a second embodiment of the invention. The dispenser 20 has substantially linear seals 14 and 22. A third circular-seal 24 is located proximate to one end. The circumference of seal 24 is smaller than the length of either of the end seals 14 and 22. The circular-seal 24 is preferably a heat seal.

To open the dispenser 20, a user squeezes it between the seal 14 and the seal 24. When the user squeezes with sufficient force, the dispenser 20 opens at seal 24. If seal 24 is a heat seal, the opening is on the weaker (thinner) side of the seal, that is, the side which was next to the heated platen. Seal 24 fails before either of the linear seals 14 and 22 fail because the stresses at each point of seal 24 are greater than the stresses at any point on either of the linear seals.

The seal 24 may be of any shape, for example, a star or a square, as long as its circumferential length is smaller than the lengths of either seal 14 or 16. The ratios of the lengths of the seals 14 and 22, respectively, and circumference of the seal 24 affect how much force a user must apply to the dispenser 20 in order to open it. If the ratios are large, the user need only apply a relatively small force to open the dispenser 20. However, if the ratios are small, the user must apply a larger force.

Figure 3:
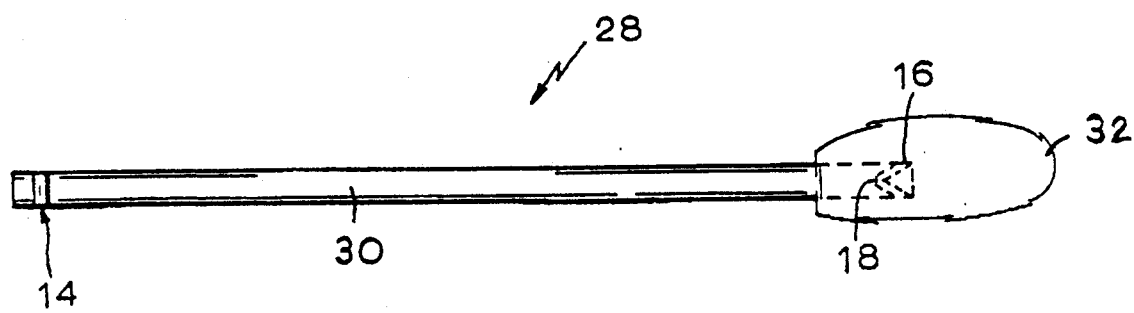
FIG. 3 is an illustration of the dispenser of FIG. 1 with a saturable covering on one end.

FIG. 3 is an illustration of an applicator 28 constructed in accordance with the preferred embodiment. The applicator 28 consists of two attached pieces, a dispenser 30 which is identical to the dispenser 10 of FIG. 1 or the dispenser 20 of FIG. 2 and a saturable end-piece 32. The saturable end-piece 32 may be made out of cotton or any other saturable material. In the preferred embodiment, the applicator 28 includes a dispenser 30 which is identical to dispenser 10 of FIG. 1.

To use the applicator 28, a user squeezes the dispenser 30 at a spot between the two heat seals 14 and 16. As discussed above with reference to FIG. 1, the dispenser 30 opens as apex 18 of the inverted V-shaped seal 16. The user continues squeezing the dispenser 30 until the fluid in the dispenser 30 saturates end-piece 32, or a portion of it. The user may then spread the fluid on a surface by rubbing the surface with the applicator end-piece 32. If the user requires additional fluid, he or she may continue to squeeze the dispenser 30 as he or she is rubbing the applicator endpiece 32 over the surface. Thus the user can apply a desired amount of fluid to a surface without contacting the fluid. Accordingly, the applicator 28 may be used to apply a sterile dosage of cream to the body, or to apply a chemical to a particular surface.

The dispensers 10 and 20 and the applicator 28 have countless uses. One specific use is in conjunction with a chemical detection kit which is the subject of a co-pending application Ser. No. 07/358,556 entitled "Chemical Detection Kit". The chemical detection kit is used to test substances for traces of a particular chemical, for example, to test paint for traces of lead.

The kit consists of a transparent, partially sealed pouch containing a porous swatch. The pouch is impregnated with a sensing chemical, in this case one that is sensitive to lead. To test a paint sample, a user introduces paint particles into the pouch and manipulates the pouch to bring the particles into contact with the swatch. The user then applies an activating agent, for example, water, to the pouch to activate the sensing chemical. Next, the user manipulates the pouch to soak the particles and the swatch. If the particles contain lead, the swatch turns a tell-tale color.

The co-pending application discusses using an eye dropper to supply the activating agent to the pouch. If water is used as the activating agent and the local water contains traces of lead, the water contaminates the test. To avoid contaminating the tests, lead-free water housed in dispensers 10 or 20 may be included in the kits. Similarly, for the convenience of the user when other activating agents are used, the activating agents may be included in the kits in dispensers 10 or 20.

If the activating agent is included in the kit in a dispenser 10, the user simply inserts the dispensing end 17 of the dispenser 10 into the pouch containing the paint particles. The user then squeezes the dispenser 10 to open it, and continues squeezing to deliver the desired amount of activating agent to the pouch. The predictable way in which the dispenser 10 opens and dispenses the fluid enables a user to control the amount of fluid supplied to the test pouch.

An applicator 28 containing a sensing chemical may be used to test for traces of a particular substance, for example, lead, in minute particles such as dust. The user wipes the dry applicator end-piece 32 along a surface supporting the dust, for example, along the floor, to pick-up the dust. The user next squeezes the dispenser 30 to open it and release the sensing chemical. If the dust contains lead, the end-piece 32 turns a tell-tale color when the released chemical contacts the dust. Thus particles which are too tiny to load into a test pouch may be tested using the applicator 28.

The foregoing description has been limited to a number of specific embodiments of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. A fluid dispenser, the dispenser including a flexible vessel for containing a fluid, the vessel including
   i. a top wall and a bottom wall, and
   ii. means comprising a seal concentrating in a region thereof forces resulting from pressure generated in the fluid by applying a force to the vessel, said seal sealing the top wall to the bottom wall, said vessel being sufficiently strong that a weaker of the top wall or the bottom wall at the seal ruptures at the region of concentration in response to the applied force to form an opening through which the fluid is dispensed.

2. The fluid dispenser of claim 1, wherein the seal is V-shaped with its apex pointing toward the center of the vessel, the apex of the seal being the region of concentration.

3. The fluid dispenser of claim 1, wherein the seal is a circular seal with a periphery which is smaller than the diameter of the vessel at the location of the seal, the edge of the circular seal being the region of concentration.

4. The fluid dispenser of claim 1, wherein the seal is a heat seal which is formed by applying heat to one of the top or bottom walls of the vessel, the wall to which the heat is applied opening at the region of concentration in response to the applied force.

5. The fluid dispenser of claim 1, wherein the dispenser further includes a fluid-absorbing applicator for topically applying the contents of the vessel to a surface, the applicator being situated so as to absorb the contents of the vessel as they flow through the opening in the vessel wall.

6. The fluid dispenser of claim 5, wherein the seal is a heat seal which is formed by applying heat to one of the top or bottom walls of the vessel and the wall to which the heat is applied opens at the apex in response to the applied force.

7. A fluid dispenser, the dispenser including a flexible vessel for containing a fluid, the vessel having a seal sealing a top wall to a bottom wall, the seal being V-shaped to concentrate at the apex of the seal forces resulting from pressure generated in the fluid by applying a force to the vessel, and the seal being sufficiently strong that a weaker of the top wall or the bottom wall at the seal ruptures at the apex in response to the applied force to form an opening through which the fluid is dispensed.

* * * * *